United States Patent [19]

Aubry et al.

[11] Patent Number: 5,750,777
[45] Date of Patent: May 12, 1998

[54] PROCESS FOR THE PREPARATION OF CARBOXYLIC ACIDS BY CONTROLLED OXIDATION OF THE CORRESPONDING ALKANES

[75] Inventors: Alain Aubry, Joinville Le Pont; Michel Gubelmann; Anne-Marie Le Govic, both of Paris, all of France

[73] Assignee: Rhone-Poulenc Chimie, Courbevoie, France

[21] Appl. No.: 579,191

[22] Filed: Dec. 27, 1995

[30] Foreign Application Priority Data

Dec. 29, 1994 [FR] France ................................ 94 15932

[51] Int. Cl.$^6$ .......................... C07C 51/18; C07C 27/10
[52] U.S. Cl. ........................... 562/549; 562/512.2
[58] Field of Search ...................... 562/549, 512.2

[56] References Cited

U.S. PATENT DOCUMENTS 4,192,951  3/1980  Slinkard ........................... 562/549
4,410,752  10/1983  Blum ................................ 585/658
5,300,682  4/1994  Blum et al. ....................... 562/549

FOREIGN PATENT DOCUMENTS 0 627 401  7/1994  European Pat. Off. ........ C07C 53/08

*Primary Examiner*—Paul J. Killos
*Attorney, Agent, or Firm*—Katherine L. Carleton

[57] ABSTRACT

The present invention relates to a process for the preparation of carboxylic acids by controlled oxidation of the corresponding alkanes.

The process according to the invention consists in reacting the alkane with a source of oxygen, the reaction being performed in the presence of a catalyst in which the active phase is based on vanadium, titanium, molybdenum, phosphorus and oxygen.

26 Claims, No Drawings

PROCESS FOR THE PREPARATION OF CARBOXYLIC ACIDS BY CONTROLLED OXIDATION OF THE CORRESPONDING ALKANES

The present invention relates to a process for the preparation of carboxylic acids by controlled oxidation of the corresponding alkanes, in the presence of a catalyst in which the active phase is based on vanadium, titanium, molybdenum, phosphorus and oxygen. More particularly, the invention relates to a process for the preparation of acetic acid by controlled oxidation of ethane.

Process for the production of saturated carboxylic acids by controlled oxidation of the corresponding alkanes, in the presence of a catalyst, are in full development because they have the advantage of using raw materials which are advantageous in cost.

Among particularly known processes for the preparation of acetic acid, there may be mentioned those involving, in addition to ethane and oxygen, complex catalysts based on at least one mixture of molybdenum, vanadium, niobium and/or antimony oxides. However, the selectivity for acetic acid when such catalysts are used is of the order of only 15 to 25%, while the reaction conditions are relatively severe. In fact, the oxidation must be carried out under conditions combining an elevated temperature, that is to say of the order of 400° C., and a pressure of at least 20 bar.

Another process consists in reacting ethane and oxygen in the presence of a catalyst based on at least vanadium, phosphorus and rhenium oxides. The selectivities for acetic acid are improved in comparison with those of the catalysts described above (of the order of 30%) but nevertheless remain lower than those for the ethylene which is also produced. In addition, this process requires large quantities of water and of a diluent such as helium or nitrogen to be introduced into the reactor.

It is known, furthermore, to employ catalysts in which the active phase includes vanadium, the latter being in the (IV) oxidation state, titanium and/or phosphorus and oxygen. In the case of these catalysts the performance is advantageous in terms of selectivity for acetic acid. On the other hand, the reaction conditions make this process impossible to exploit on an industrial scale. In fact, the conversion of ethane is low and the feed flow includes more than 90% of diluent gas, and this results in a very low output efficiency.

Another type of catalytic composition has been described making it possible to obtain acetic acid by oxidation of ethane with advantageous performance. However, it appears that this performance is achieved by employing relatively severe reaction conditions, since the pressure is close to 30 bar and the temperature is close to 300° C. In addition, the catalytic composition in question includes no fewer than six elements and the preparation process is particularly complex and difficult to control in terms of arrangement of the species relative to one another in the finished catalyst. In fact, synthesis of the said catalyst consists in preparing various solutions including, for the most part, a single constituent element, then in evaporating the solvent. Such a method may lead to catalysts whose performance is not perfectly reproducible from one catalyst to another.

Thus, as can be ascertained, at the present time there are no processes for the preparation of carboxylic acids by oxidation of the corresponding alkane which can be developed on an industrial scale and which make use of catalysts whose synthesis is simple and controlled.

Now, it has been found quite unexpectedly that the use of catalysts based on vanadium, titanium, molybdenum, phosphorus and oxygen, in the aforementioned reaction, made it possible to mitigate the disadvantages referred to above.

An additional advantage of the process according to the invention resides in the relatively low activation temperature of the alkane, and more particularly ethane. In fact, the conventional temperatures necessary for the activation of hydrocarbons in oxidation reactions, such as the oxidation of propylene, of orthoxylene and of butane are close to 400° C. Knowing that olefins are more reactive than alkylaromatic compounds, which are themselves much more reactive than alkanes, and that, furthermore, the reactivity of saturated hydrocarbons increases with the number of carbon atoms present in the molecule, it is entirely surprising that it is possible to activate ethane at temperatures which may be as low as 150° C.–275° C.

Furthermore, and this represents another surprising advantage, the activation period of the catalyst used according to the invention is much shorter than for the catalysts employed in conventional processes, even though the activation temperature is much lower than in conventional processes.

These objectives, and others, are met by the present invention which therefore relates to a process for the preparation of carboxylic acid by a gas phase reaction of the corresponding alkane with a source of oxygen, in the presence of a catalyst in which the active phase includes vanadium, titanium, molybdenum, phosphorus and oxygen.

For greater convenience the catalyst used in the invention will be described first of all.

As mentioned above, the active phase of the catalyst used includes vanadium, titanium, molybdenum, phosphorus and oxygen.

According to a more particular embodiment of the invention, the active phase of the catalyst corresponds to the following formula: $P_aMo_bV_cTi_dO_x$; in which the stoichiometric coefficients satisfy the following relationships: $b+c+d=1.0$; $0.9<(a/c)<3$; $0.5<d<0.99$; and $0.01<(c/b+c)<0.92$.

Preferably, the aforementioned stoichiometric coefficients satisfy the following relationships: $b+c+d=1.0$; $1.0<(a/c)<2.2$; $0.7<d<0.98$; and $0.08<(c/b+c)<0.6$.

The active phase of the catalyst used in the process of the invention may furthermore include a dopant.

The dopant is more particularly chosen from the following elements: K, Rb, Cs, Ca, Mg, Zr, Hf, Nb, Ta, Cr, W, Mn, Re, Fe, Ru, Os, Co, Rh, Ir, Ni, Pd, Cu, Ag, Zn, Cd, Tl, Si, Ge, Sn, As, Sb, Bi, Ga and the rare earths.

Preferably the dopant is chosen from the following list: K, Cs, Zr, Nb, Ta, Cr, W, Mn, Re, Fe, Ru, Co, Pd, Ag, Zn, Tl, Sb, Bi, Ga, Sn, La and Ce.

Usually, the quantity of dopant in the active phase is such that the ratio of the dopant to vanadium is between 0.005 and 0.10, and preferably between 0.009 and 0.06.

The catalyst used in the process of the invention may be in a bulk form, that is to say essentially include the active phase described above, or else be in a diluted form.

In the particular case when the catalyst includes a diluent (or support) the active phase may either be deposited on the latter or may coat it or else may be mixed with it.

The nature of the diluent is not critical, except that it must be inert towards the reactants under the reaction conditions which are chosen.

By way of materials capable of being employed as catalyst support there may be mentioned: silica, alumina, silica-alumina, sintered clay, magnesia, magnesium silicate and diatomaceous earth. Supports of this type can be employed in porous or nonporous form. The support employed is preferably in nonporous form. If need be, a glazing of these may be performed in order to make it such.

Ceramic materials, of the cordierite, alumina, mullite, porcelain, silicon nitride and boron and silicon carbide type may also be employed as a diluent.

The catalyst used in the process according to the invention, whether diluted or not, is in particle or monolithic form.

In the case when the catalyst consists of particles, the size of these particles depends on the method of use of the catalyst. It may therefore vary within wide limits and may, in particular, be between a few micrometers and of the order of ten millimeters. More particularly, by way of indication, a catalyst employed in a stationary bed has a particle size distribution which is generally between 0.5 and 6 mm. The size of the particles of a catalyst employed in a fluidized or moving bed is usually between 5 and 700 microns and preferably between 5 and 200 microns for 80% of the particles.

The quantity of diluent forming part of the composition of the catalyst conventionally varies within wide limits depending, most of the time, on the method of formation of the catalyst.

Thus, catalysts obtained by coating or depositing the active phase on the support have a quantity of active phase which usually varies between 0.1 and 30%, and preferably between 2 and 20%, of the total weight of finished catalyst (active phase and support).

In the cases when the catalyst includes a support dispersed in the active phase, the quantity of active phase is generally between 1 and 90% of the total weight of finished catalyst.

According to a particular embodiment of the invention, the reaction is performed in the presence of a catalyst of the coated type.

The active phase of the catalyst used in the present invention can be obtained by any method known to the person skilled in the art.

It is possible, for example, to envisage manufacturing the said active phase by mixing the oxides of the constituent elements of the active phase, followed by a calcination stage, optionally followed and/or preceded by grinding of the said mixture (grog technique).

Another method which is suitable for the preparation of the active phase consists in drying a solution of the constituent elements of the active phase, followed by a calcination. It may similarly be envisaged to carry out this drying operation on a suspension of the said constituent elements, this suspension originating from the use of at least one of these elements in the form of a solid, or else originating from an intermediate step of precipitation, or of controlled hydrolysis of one or more alkoxides, for example.

The term constituent elements means not only vanadium, titanium, phosphorus and molybdenum, but also the dopant or dopants added to the composition of the active phase.

The constituent elements are usually employed in the form of a solution or of a suspension.

The dispersing (or solubilizing) medium is advantageously water, although any other type of dispersant (or solvent) can be envisaged. Alcohols such as methanol, ethanol, isopropanol and tert-butanol may, in particular, be mentioned under this heading.

The constituent elements of the active phase forming part of the composition of the aforementioned mixture are generally employed in the form of salts of inorganic or organic acids or bases, or else in the form of compounds such as oxides or their derivatives.

All the acids or derivatives of oxides indicated are suitable for the preparation of the mixture, in so far as they can decompose to an oxide of the corresponding element or elements.

By way of examples of inorganic salts which are suitable for the preparation of the aforementioned mixture there may be mentioned, among others, nitrates, sulphates, halides including one or more halogens and ammonium salts.

By way of examples of salts of organic acids or esters there may be mentioned formate, oxalate, tartrate, acetate, acetylacetonate and ethylhexanoate.

As already indicated, it can also be envisaged to employ oxides or their derivatives, it being possible for these compounds to be used in the form of particles, or dissolved, especially by adding an acid or a base to the said mixture.

The term oxide derivatives is intended to mean compounds of the oxyhalide, alkoxide, aryloxide and glycoxide type, in particular.

It should be noted that these types of compounds can be employed by themselves or mixed.

By way of examples of compounds including vanadium and suitable for making use of this method of preparation there may be mentioned, without any limitation being intended, vanadyl sulphate, ammonium metavanadate, vanadium oxyhalides such as, in particular, $VOCl_3$, $(VO_2)Cl$, $VOCl$, $VOBr$, $VOBr_2$, $VOF_3$, $VOF_2$, $VF_4$, $VBr_2$, $VI_2$, vanadyl acetylacetanoate, vanadyl oxalate, metavanadic acid, vanadium hexacarbonyl, vanadium oxide triisopropoxide and vanadium oxides such as, for example, $V_2O_5$, $V_7O_{13}$, $VO$, $VO_2$, $V_2O_3$, $V_3O_7$, or mixtures thereof.

As a compound including titanium there may be mentioned compounds of the $TiX_4$ type with X denoting a halogen and more particularly chlorine, and compounds of the $Ti(OR)_4$, type with R denoting an alkyl group and more particularly the ethyl, isopropyl or sec-butyl radicals.

Titanium oxide in its various allotropic forms, that is to say in anatase, rutile, brookite or bronze (symbolically represented (B)), form, or mixtures thereof, are also suitable for making use of the invention. Preferably, the allotropic form of titanium oxide is chosen from the anatase and rutile forms or mixtures thereof.

If synthesis of the active phase is carried out with a titanium oxide, a titanium oxide is more especially employed whose specific surface, measured by the B.E.T. method, is between 1 and 150 m²/g. More particularly, the specific surface is between 10 and 120 m²/g.

Among molybdenum-based compounds which may be suitable for the invention there may be mentioned, in particular, ammonium dimolybdate, ammonium heptamolybdate, ammonium paramolybdate and dioxomolybdenum acetylacetonate.

As regards phosphorus-based compounds there may be mentioned, by way of example, phosphoric acids such as orthophosphoric acid, pyrophosphoric acid, metaphosphoric acid and polyphosphoric acid, alkyl phosphates such as methyl, ethyl and butyl, and ammonium phosphates.

The compounds providing the element or elements used as dopants may, in particular, be chosen from potassium chlorides, potassium acetate, rubidium chlorides, niobium chloride or oxychloride, niobium oxalate, cesium sulphate, cesium acetate, iron sulphate, iron acetate, chromium chlorides or chlorates, chromium nitrates, chromium acetate, chromium acetylacetonate and ammonium metatungstate and paratungstate, zirconium oxides and alkoxides, such as ethoxide, and silver oxide.

These lists cannot, of course, be considered as exhaustive.

According to a particular embodiment of the invention, titanium is used in the form of an oxide. In this case, at least one impregnation of the oxide with at least one solution including the constituent elements of the active phase is carried out. It is thus possible to carry out a single impregnation operation or a succession of impregnation steps. The impregnation operations are carried out in a manner which is known per se. However, at least one dry impregnation step is more particularly used. This means that the total volume of the impregnation solution used must be equal to the total pore volume of the solid to be impregnated.

All the constituent elements of the catalytic phase can be brought into contact with the support simultaneously or successively.

According to a first variant, the support is brought into contact with the constituent elements other than phosphorus, these elements being supplied in any order, simultaneously or successively. The whole is then impregnated with a solution supplying the phosphorus.

A second variant consists in carrying out the reverse procedure. Thus, firstly, one or more operations of impregnating titanium oxide with a solution including phosphorus is or are carried out, followed by at least one step of impregnation with the remaining elements, it being possible for the latter to be supplied with separate solutions simultaneously or successively, or else with the same solution.

Of course, it is possible to introduce the phosphorus compound between each of the impregnations with the molybdenum and vanadium compounds.

One or more drying steps are then carried out.

Depending on the method used for bringing the constituent elements into contact, the drying is carried out in essentially one or two steps.

Thus, in the case when the process for the preparation of the catalytic phase uses suspensions or solutions, this drying is carried out in two steps, the first consisting in evaporating the solvent or dispersant from the mixture, to dryness, and the second in drying the paste thus obtained. Generally, the first step is carried out at a temperature ranging from 20° to 100° C. for the period of time necessary to obtain a nonflowing paste. The evaporation is usually carried out with stirring.

The resulting paste is then dried, in a second step, under a preferably nonreducing atmosphere, such as, for example, oxygen or air, for an average period of 15 hours.

The drying temperature is usually approximately 120° C.

Carrying out spray drying, which method is well known to the person skilled in the art, would not depart from the scope of the invention. Thus, without any limitation being intended, the sprayers of the Buchi type or sprayers of the "flash" type, as claimed in French Patent Applications published under the following numbers: 2 257 326, 2 419 754, 2 431 321, are suitable for this embodiment. The spraying temperature is generally of the order of 150° to 300° C. The atmosphere under which the spraying is carried out, here again, is preferably nonreducing. The spraying is advantageously carried out in air, although oxygen can be envisaged for such a step.

In the case when the constituent elements of the active phase were brought into contact by dry impregnation, the drying is carried out in a single step corresponding to the aforementioned second step of the preceding variant. It should be noted that an intermediate drying step is preferably carried out after each dry impregnation operation.

The dried product obtained, regardless of the method used, is then subjected to a calcination step.

This is carried out, conventionally, under a nonreducing atmosphere. Air is advantageously employed, but oxygen might indeed also be employed.

The calcination temperature is usually between 200° and 1200° C.

The duration of the operation generally ranges between 1 and 24 hours.

Prior to the calcination step, the dry product may undergo a grinding step. It is furthermore specified that the calcined product may optionally also undergo such a treatment.

As mentioned before, the catalyst used in the process according to the present invention may or may not include a diluent (or support) coated or mixed with the active phase.

Conventionally, the quantity of diluent forming part of the composition of the catalyst varies within wide limits depending, most of the time, on the method of formation of the catalyst.

The catalyst according to the invention can be obtained by any conventional method known to the person skilled in the art.

Thus, bulk catalysts, essentially including the active phase as defined above can be formed by extrusion, by moulding, by grinding, crushing or any other means, of the active phase or of its precursor, so as to give a monolith or else particles of suitable size.

Here and throughout the remainder of the description the term precursor of the active phase is intended to mean the mixture of the constituent elements of this phase in all the states prior to the calcination step described above.

In the case of catalysts including a diluent, the means described above can be employed. The active phase can thus be mixed with the required proportion of diluent and, for example, the resulting mixture can be extruded or moulded.

However, other methods can be envisaged.

Thus, according to a first embodiment, the diluent, preferably in the form of rough particles, and the active phase or its precursor are brought into contact in a high-shear mixer (apparatus of the Lodige type) or in a granulating apparatus (pelletizers in the form of a drum or dish).

The operation is generally carried out at a temperature ranging between 20° and 150° C. for the period of time necessary for coating the support with the desired quantity of active phase, more particularly under air, for at least 30 minutes.

The particles thus obtained are usually calcined at a temperature of between 300° and 600° C., preferably between 450° and 500° C.

The calcination period is generally at least 3 hours.

A second possible method of manufacture of the catalyst consists in applying the impregnation technique.

According to this technique the support is impregnated with a suspension of the active phase or with a suspension or solution of its precursor.

The impregnation step is followed by a drying step, usually carried out at a temperature between 100° and 200° C., under air, for at least 30 minutes.

The impregnation-drying cycle can then be repeated and finished by calcining in air.

The calcination temperature is between 400° and 600° C. for of the order of ten hours.

A possible variant consists in carrying out a calcination between the impregnation-drying cycle or cycles.

According to a third method of preparation of the catalyst, the support, preferably in the form of particles, is added to the mixture of at least one of the constituent elements of the active phase. The mixture thus obtained is then treated in accordance with the various embodiments of the process for the preparation of the catalytic phase, as described above.

All these methods of preparation are, of course, given merely by way of indication and cannot in any case constitute an exhaustive list.

The present invention furthermore relates to a process for the preparation of carboxylic acids by a gas phase reaction of the corresponding alkanes with a source of oxygen, in the presence of a catalyst as defined above.

More particularly, the present invention is designed for obtaining saturated carboxylic acids having 1 to 4 carbon atoms from the corresponding alkane. The term alkane is intended to mean saturated hydrocarbons having 1 to 4 carbon atoms, the latter being optionally substituted by one or more halogen atoms.

Advantageously, the process according to the invention makes it possible to obtain acetic acid by reaction of ethane.

There are no special conditions relating to the quality of the alkane used. However, for obvious reasons of separation of the acid formed, it is preferred to employ an alkane which has a purity of at least 90%.

The latter can be employed equally well by itself or diluted in a diluent gas which is inert under the conditions of the reaction. Rare gases such as, in particular, helium or argon, or else nitrogen are diluent gases suitable for carrying out the process according to the invention.

The controlled oxidation reaction of the alkane is used in the presence of a source of oxygen. The latter may be based on pure oxygen or oxygen diluted in an inert gas. The oxidation reaction can thus be carried out by employing air as a source of oxygen.

According to a particular embodiment of the present invention, the molar ratio of the alkane to oxygen is less than 20. More particularly, this ratio is between 0.01 and 0.2 or between 0.6 and 15.

According to a preferred method of the invention, the said ratio is between 0.6 and 15.

One variant of the process consists in employing a gaseous mixture including water in addition to the other constituents.

The composition of the gaseous mixture, i.e. the alkane, the source of oxygen, if appropriate the diluent gas and the water, can vary within wide limits.

Unless stated otherwise, all the percentages indicated below are expressed relative to the total number of moles of the gaseous mixture.

In general, the ethane content in the gaseous mixture is between 0.1 and 99.9%.

According to a particular embodiment of the invention, the composition of the gaseous mixture is such that it lies outside the region of explosiveness of the said mixture.

Thus, in order to have a gaseous mixture whose composition is conveniently outside the explosiveness region, the said alkane content is more particularly between 0.1 and 3% or between 10 and 99%.

Preferably, the alkane content in the aforementioned gaseous mixture is between 10 and 99%.

The oxygen content in the gaseous mixture used similarly varies within a wide concentration range. It is, in fact, between 0.1 and 99.9%.

According to a more particular embodiment, the oxygen content in the gaseous mixture varies between 1 and 90% or between 97 and 99.9%.

The oxygen contained in the said mixture is preferably between 1 and 90%.

The water content in the gaseous mixture used is between 0 and 70%.

According to a particular embodiment, the water content in the aforementioned mixture is from 0 to 20%.

The content of diluent gas in the mixture usually varies between 0 and 70%.

More particularly, the mixture comprises between 0 and 20% of diluent gas.

The gaseous mixture is therefore brought into contact with the catalyst according to the invention.

The device in which the process according to the invention is used forms part of the conventional devices for gas phase catalytic reactions, it being possible for these to be employed continuously or noncontinuously.

The reaction can thus be carried out in the presence of a catalyst in a stationary, fluidized or else transported bed.

The reaction temperature is generally between 100° and 350° C., preferably between 150° and 330° C.

The total pressure of the gaseous reaction mixture generally ranges between 0.1 and 30 bar absolute. More particularly, the pressure ranges between 0.1 and 20 bar absolute. Preferably, and advantageously, the pressure used in the reaction is between 1.1 and 10 bar absolute.

The gas flow rate is set so that the contact time, calculated under normal temperature and pressure conditions, is between 0.1 and 30 seconds. The contact time is preferably between 0.5 and 20 seconds. It should be remembered that the contact time corresponds to the ratio between the volume of the reactor and the total flow rate of the gases.

The acid formed is separated from the by-products or the reactants, conventionally by cooling and then condensing an acid/water mixture. The compounds which remain in gaseous form, more particularly the alkane, can be recycled to the reactor after having optionally been subjected to a separation step.

Concrete but nonlimiting examples of the invention will now be presented.

COMPARATIVE EXAMPLE 1

Preparation of the catalyst 1

90 g of $TiO_2$ (i.e. 1.125 mol), exhibiting a BET surface equal to 86 m$^2$/g (marketed by Rhône Poulenc) are introduced into a pelletizer and impregnated dry with 100 cm$^3$ of a solution of vanadyl oxalate.

The solution employed includes 15.23 g of oxalic acid dihydrate (i.e. 120.8 mmol) and 6.77 g of $V_2O_5$ marketed by Janssen (i.e. 37.2 mmol) in water.

The product thus obtained is calcined for 3 hours in air at 500° C.

The composition of the calcined product has 7% by weight of $V_2O_5$ and a V/Ti ratio of 0.066.

COMPARATIVE EXAMPLE 2

Preparation of the catalyst 2

3.15 g of tartartic acid is dissolved in the hot state with stirring in 17 ml of deionized water. After dissolving, 1.40 g of $V_2O_5$ in powder form are added to the solution. This compound is dissolved in the hot state and with stirring.

Once a solution has been obtained, it is allowed to return to room temperature and 2.03 g of orthophosphoric acid at 85% is added to it.

45 g of titanium dioxide in anatase form (specific surface: 45 m$^2$/g, total pore volume: 0.38 cm$^3$/g) are then impregnated with this solution in a rotating pelletizer.

The powder obtained is dried in air for 6 hours at 150° C. then calcination is carried out for 3 hours in air at 400° C.

A solid having an atomic ratio P/V/Ti=0.031/0.027/1 is thus obtained.

EXAMPLE 3

Preparation of the catalyst 3

A mixture of 16.8 g of ammonium heptamolybdate of formula $(NH_4)_6Mo_7O_{24}$ (i.e. 0.095 mol of Mo) and 1.11 g of ammonium metavanadate of formula $NH_4VO_3$ (i.e. 0.0095 mol of V) are dissolved at reflux, with stirring, in a volume of 70 cm$^3$ of deionized water.

The yellow solution obtained is cooled and its volume is adjusted to 80 cm$^3$.

This solution is used for dry impregnation of 50 g of $TiO_2$ anatase having a specific surface of 80 m$^2$/g and a pore volume of 0.8 cm$^3$/g (i.e. 0.625 mol of Ti).

The impregnation is carried out in two steps, with the use of 40 cm$^3$ of solution in each operation and intermediate drying at 110° C.

Dry impregnation of the resulting solid with 40 cm$^3$ of an aqueous solution of phosphoric acid containing $9.52 \times 10^{-3}$ mol of $H_3PO_4$ is then carried out.

After drying at 110° C. in air, calcination of the resulting solid is carried out at 400° C. for 2 hours in air.

A solid having an atomic ratio P/Mo/V/Ti=0.015/0.153/0.014/1 is thus obtained.

EXAMPLE 4

Use of the catalysts

This example illustrates the application of the catalysts prepared above in a process for the preparation of acetic acid from ethane.

1 to 3 grams of catalyst in ground powder form (particle size less than 200 μm) are introduced into a Hastelloy C22 stationary-bed continuous reactor. The volume of the resulting catalytic bed is 5 cm$^3$, this value being obtained, if need be, by diluting the catalyst with silicon carbide with the same particle size. The dead volumes upstream and downstream of the catalytic bed are also lined with silicon carbide.

The reactor is equipped with a heating system using a fluidized sand bath and two in-line chromatographs, one operating with a flame ionization detector and the other with a katharometer detector.

The feed gases are controlled by mass flow meters.

The water is introduced in liquid form (Gilson metering pump) into a vapourizer integrated into the gas circuit.

The feed flow consists of:

$C_2H_6/O_2/N_2/H_2O$=62/17/10/12 mol %.

The ethane flow rate, relative to the mass of catalyst used, is 2.0 g/l/h under normal temperature and pressure conditions.

The temperature is 275° C.

The results obtained are collated in the following table.

In this table, the performance is calculated as follows:

—ethane conversion (mol %)

$$\text{ethane } conv. = \frac{\text{(no. moles ethane in − no. moles ethane out)}}{\text{(no. moles ethane in)}} \times 100$$

—selectivity for a product X (acetic acid, ethylene, comb products) (mol %)

$$x \, sel. = \frac{\text{(no. moles ethane converted into } X\text{)}}{\text{(no. moles ethane in − no. moles ethane out)}} \times 100$$

| CATALYST | P (bar abs.) | ETHANE CONVERSION (%) | SELECTIVITY (%) | | |
|---|---|---|---|---|---|
| | | | acetic acid | ethylene | combustion products |
| 1 comparative | 1 | 0.3 | 5 | 40 | 55 |
| | 7 | 2.2 | 15 | 20 | 65 |
| 2 comparative | 1 | 0.7 | 17 | 33 | 49 |
| | 6 | 3.6 | 20 | 18 | 61 |
| 3 invention | 1 | 1.0 | 28 | 33 | 39 |
| | 6.3 | 6.5 | 38 | 11 | 51 |

What is claimed is:

1. A process for the preparation of carboxylic acids comprising a gas phase reaction of the corresponding alkane with a source of oxygen, wherein said reaction is performed in the presence of an effective oxidation catalytic amount of a catalyst in which the active phase comprises vanadium, titanium, molybdenum, phosphorus and oxygen.

2. The process according to claim 1, wherein said active phase is of the following formula:

$P_aMo_bV_cTi_dO_x$ in which the stoichiometric coefficients satisfy the following relationships:

b+c+d=1.0;
0.9<(a/c)<3;
0.5<d<0.99; and
0.01<(c/b+c)<0.92.

3. The process according to claim 2, wherein the stoichiometric coefficients satisfy the following equations:

b+c+d=1.0;
1.0<(a/c)<2.2;
0.7<d<0.98; and
0.08<(c/b+c)<0.6.

4. The process according to claim 1, wherein said catalyst is employed in bulk or diluted form.

5. The process according to claim 1, wherein said catalyst is coated and the quantity of said active phase is between about 0.1 and about 30% by weight of the total weight of the catalyst.

6. The process according to claim 5, wherein the quantity of said active phase is between about 2 and about 20% by weight.

7. The process according to claim 4, wherein said catalyst comprises a support dispersed in the active phase, said active phase being between about 1 and about 90% by weight of the total weight of the catalyst.

8. The process according to claim 1, wherein the active phase furthermore includes one dopant selected from the group consisting of : K, Rb, Cs, Ca, Mg, Zr, Hf, Nb, Ta, Cr, W, Mn, Re, Fe, Ru, Os, Co, Rh, Ir, Ni, Pd, Cu, Ag, Zn, Cd, Tl, Si, Ge, Sn, As, Sb, Bi, Ga, the rare earths and the possible mixtures thereof.

9. The process according to claim 8, wherein the dopant content is such that the ratio of the dopant to vanadium is between about 0.005 and about 0.10.

10. The process according to claim 9, wherein the ratio of the dopant to vanadium is between about 0.009 and about 0.06.

11. The process according to claim 1, wherein said reaction is performed with a gaseous mixture including bout 0.1 to about 99.99 mol % of alkane.

12. The process according to claim 11, wherein said gaseous mixture includes between about 10 and about 99 mol % of alkane.

13. The process according to claim 11, wherein said gaseous mixture includes between about 0.1 and about 3 mol % of alkane.

14. The process according to claim 1, wherein said source of oxygen is air or oxygen.

15. The process according to claim 1, wherein the reaction is performed with a gaseous mixture comprising about 0.1 to about 99.9 mol % of oxygen.

16. The process according to claim 15, wherein said gaseous mixture comprises between 1 and about 90 mol % of oxygen.

17. The process according to claim 15, wherein said gaseous mixture comprises between about 97 and about 99% of oxygen.

18. The process according to claim 15, wherein said gaseous mixture has an alkane/oxygen molar ratio less than about 20.

19. The process according to claim 18, wherein said alkane/oxygen molar ratio is between about 0.6 and about 15.

20. The process according to claim 18, wherein said alkane/oxygen molar ratio is between about 0.01 and about 0.2.

21. The process according to claim 1, wherein the reaction is performed with a gaseous mixture comprising water.

22. The process according to claim 21, wherein said gaseous mixture comprises up to about 70 mol % of water.

23. The process according to claim 21, wherein said gaseous mixture comprises up to about 20 mol % of water.

24. The process according to claim 1, wherein the reaction is performed with a gaseous mixture comprising a diluent gas chosen from the rare gases or nitrogen.

25. The process according to claim 24, wherein said gaseous mixture comprises up to about 70 mol % of said diluent gas.

26. The process according to claim 25 wherein said gaseous mixture comprises up to 20 mol % of said diluent gas.

* * * * *